United States Patent
Bales et al.

(10) Patent No.: US 6,570,175 B2
(45) Date of Patent: May 27, 2003

(54) INFRARED IMAGING ARRANGEMENT FOR TURBINE COMPONENT INSPECTION SYSTEM

(75) Inventors: Maurice J. Bales, Lafayette, CA (US); Dimitry S. Vladimirov, Daly City, CA (US); Brian A. Dalio, Lake Oswego, OR (US)

(73) Assignee: Computerized Thermal Imaging, Inc., Lake Oswego, OR (US)

( * ) Notice: Subject to any disclaimer, the term of this patent is extended or adjusted under 35 U.S.C. 154(b) by 0 days.

(21) Appl. No.: 10/062,631

(22) Filed: Jan. 31, 2002

(65) Prior Publication Data

US 2003/0080297 A1 May 1, 2003

Related U.S. Application Data

(60) Provisional application No. 60/339,724, filed on Nov. 1, 2001.

(51) Int. Cl.[7] ................................................ G01N 21/86
(52) U.S. Cl. ................................ 250/559.4; 250/559.45
(58) Field of Search ........................ 250/559.4, 559.45, 250/559.42, 559.33, 216, 223 R, 223 B, 338.1, 341.8, 208.1, 221; 356/73, 430, 428, 237.1, 239.4, 239.5, 239.7, 239.8

(56) References Cited

U.S. PATENT DOCUMENTS

| | | | |
|---|---|---|---|
| 4,644,162 A | | 2/1987 | Bantel et al. |
| 5,045,688 A | * | 9/1991 | Domenico et al. ...... 250/223 B |
| 5,111,046 A | | 5/1992 | Bantel |
| 5,625,196 A | | 4/1997 | Williams |
| 6,308,914 B1 | | 10/2001 | Spurway et al. |

* cited by examiner

Primary Examiner—Que T. Le
(74) Attorney, Agent, or Firm—Schwabe, Williamson & Wyatt, P.C.

(57) ABSTRACT

An improved infrared (IR) imaging arrangement for a turbine component inspection system includes a platform having a turbine component base feature to receive a turbine component for inspection. Disposed on the platform are a number of mirrors around the turbine component feature. The number of mirrors simultaneously reflects a number of sides/edges for detection by an IR imager. As a result, the IR imager simultaneously view more than one sides/edges of a turbine component.

32 Claims, 4 Drawing Sheets

INFRARED IMAGING ARRANGEMENT FOR TURBINE COMPONENT INSPECTION SYSTEM

RELATED APPLICATION

This patent application claims benefit of priority to provisional patent application No. 60/339,724, titled "AN IMPROVED INFRARED IMAGING ARRANGEMENT FOR TURBINE COMPONENT INSPECTION SYSTEM", filed Nov. 01, 2001.

FIELD OF THE INVENTION

The invention relates to the field of infrared (IR) inspection of turbine components, such as turbine blades, turbine vanes, and other turbine items of the like and passages and/or cooling channels for liquid or gas flow. More specifically, the invention relates to simultaneously inspecting more than one side of a turbine blade, while providing protection to an IR imager.

BACKGROUND OF THE INVENTION

Manufacturing a turbine component may involve casting and machining processes, and each of these processes may introduce variables that affect quality of the component. Controlling the quality of the component is important because the quality of the component may affect its performance.

During the casting process, variables such as core misalignment, inclusions, and the like, can introduce casting defects into the blade. Often times, these casting defects may affect the machining process resulting in machining defects, as well. An example of a turbine component may be a thin or flat object that may be referred to as vanes or blades utilized to cause fluid flow or direct fluid.

For example, a gas turbine blade may include features such as cooling channels and holes. Cooling channels are internal features of the blade through which gases may flow. Because of the internal nature of the cooling channels, cooling channels are, often times, formed during the casting process utilizing casting cores. Defects, such as core misalignments may result in incorrectly formed or blocked cooling channels.

The cooling holes allow the gas flowing through the blade to be exhausted out of the blade. The dimension of the cooling holes may be in the range of 10ths of millimeters. Because of the small dimension of the cooling holes, often times, the cooling holes are machined into the blade after the casting process. In order to control the precision of machining the cooling holes, an automated process may be utilized for the physical drilling of the holes, such as computerized numerically controlled (CNC) machine.

Drilling the cooling holes by CNC machine involves the CNC machine determining the exact position of the cooling holes in three-dimensional space accounting for dimensional tolerances. If casting defects, such as core misalignments, affect the dimensions of the blade to the extent that the dimensional tolerances are exceeded, the cooling holes may not be drilled properly.

Recently, inspection methods involving thermal signatures of materials are being utilized, in particular, infrared (IR) detection imaging. An inspection method utilizing IR imaging involves applying a thermal differential to a turbine component. Often times, applying a thermal differential involves delivering a thermal stimulus, such as a gas, at a high temperature to the blade, and then, immediately following the high temperature thermal stimulus, delivering another thermal stimulus, such as the gas, at a cold temperature (i.e., cold, relative to the high temperature thermal stimulus) to the turbine component. Often times, in inspecting a turbine component, hot and cold gases are used as the inspection medium for delivering thermal stimuli. An example of an IR inspection apparatus may be found in co-pending U.S. patent application Ser. No. 10/062,638 titled "TURBINE COMPONENT INSPECTION SYSTEM", contemporaneously filed, and having common inventorship with present application. The application is incorporated herein in its entirety by reference.

In order to generate high quality images from the IR imager, the IR imager views the turbine component when the turbine component is at its optimum temperatures. However, due to the principles of heat transfer, the optimum temperatures may only last for a couple of seconds. Under the prior art, if more than one side of the turbine component is to be viewed, the IR imager is repositioned and the inspection cycle repeated. Repeating the inspection cycle for the same turbine component may introduce variables, such as thermal gradients, that may adversely affect the results of each inspection for the same turbine component. Further, the features of interest on a turbine component may be on various surfaces, and certain features may require viewing from more than one side of the turbine component.

More than one IR imager could be used to simultaneously view more than one side during an inspection; however, multiple IR imagers would add cost and complexity to the IR inspection apparatus.

BRIEF DESCRIPTION OF THE DRAWINGS

The invention is illustrated by way of example and not by way of limitation in the figures of the accompanying drawings, in which the like references indicate similar elements and in which.

DETAILED DESCRIPTION OF THE INVENTION

In the following description, various aspects of the invention will be described. However, it will be apparent to those skilled in the art that the invention may be practiced with only some or all described aspects. For purposes of explanation, specific numbers, materials and configurations are set forth in order to provide a thorough understanding of the invention. However, it will also be apparent to one skilled in the art that the invention may be practiced without the specific details. In other instances, well-known features are omitted or simplified in order not to obscure the invention.

Various operations will be described as multiple discrete steps in turn, in a manner that is most helpful in understanding the invention. However, the order of description should not be construed as to imply that these operations are necessarily order dependent. In particular, these operations need not be performed in the order of presentation.

In various embodiments of the present invention, an infrared (IR) inspection apparatus that facilitates simultaneously viewing of more than one side of an inspection article by an IR imager, while protecting the IR imager from high temperature gases and debris, is disclosed. This and other advantages will be evident from the disclosure.

Figures 1A, 1B:
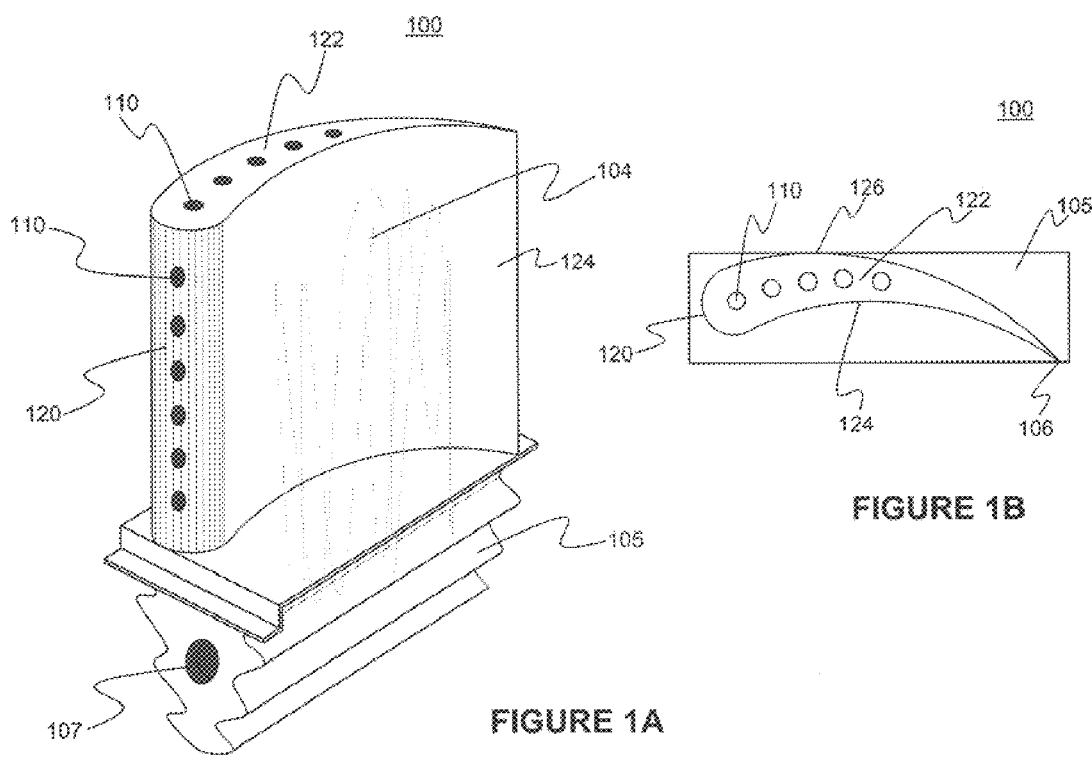
FIGS. 1A–1B illustrate a perspective view and a top view of an exemplary article for inspection upon which one embodiment of the present invention may be practiced.

FIGS. 1A–1B illustrate a perspective view and a top view of an exemplary object for inspection upon which one embodiment of the present invention may be practiced. Shown in FIGS. 1A–1B, the object is a turbine component, in particular, an exemplary turbine blade 100. Shown in FIG. 1A, the exemplary turbine blade 100 includes a base 105 having an inlet 107 to receive an inspection medium, such as, but not limited to gas, for delivery of thermal stimulus. The gas may be alternating gases at complementary temperatures, such as, but not limited to, hot and cold gases respectively. Also shown in FIG. 1A, are internal cooling channels 109 within the blade 100 through which the gas flows. The gas is exhausted from the blade 100 through cooling holes 110. As shown in FIG. 1A, the cooling holes 110 may be on different surfaces, a leading edge 120 and a blade end 122. Also shown in FIG. 1B is a pressure side 124, and a trailing edge 106.

Referring now to FIG. 1B, shown is a top view with the various sides/edges labeled. The sides of interest for inspection can be the leading edge 120, the pressure side 124, and the suction side 126. The edges of interest for inspection can be the leading edge 120 and the trailing edge 106. In various inspection applications, the two sides 124 & 126 and the two edges 120 & 106 are required to be viewed simultaneously by an IR imager during an inspection.

In FIGS. 1A–1B, the turbine component illustrated is a blade type, but it should be appreciated by those skilled in the relevant art that teachings of the present invention may be practiced with any high precision turbine component having features such as, but not limited to, cooling holes or channels. For ease of understanding the invention, the turbine component illustrated is the blade 100.

Figure 2A:
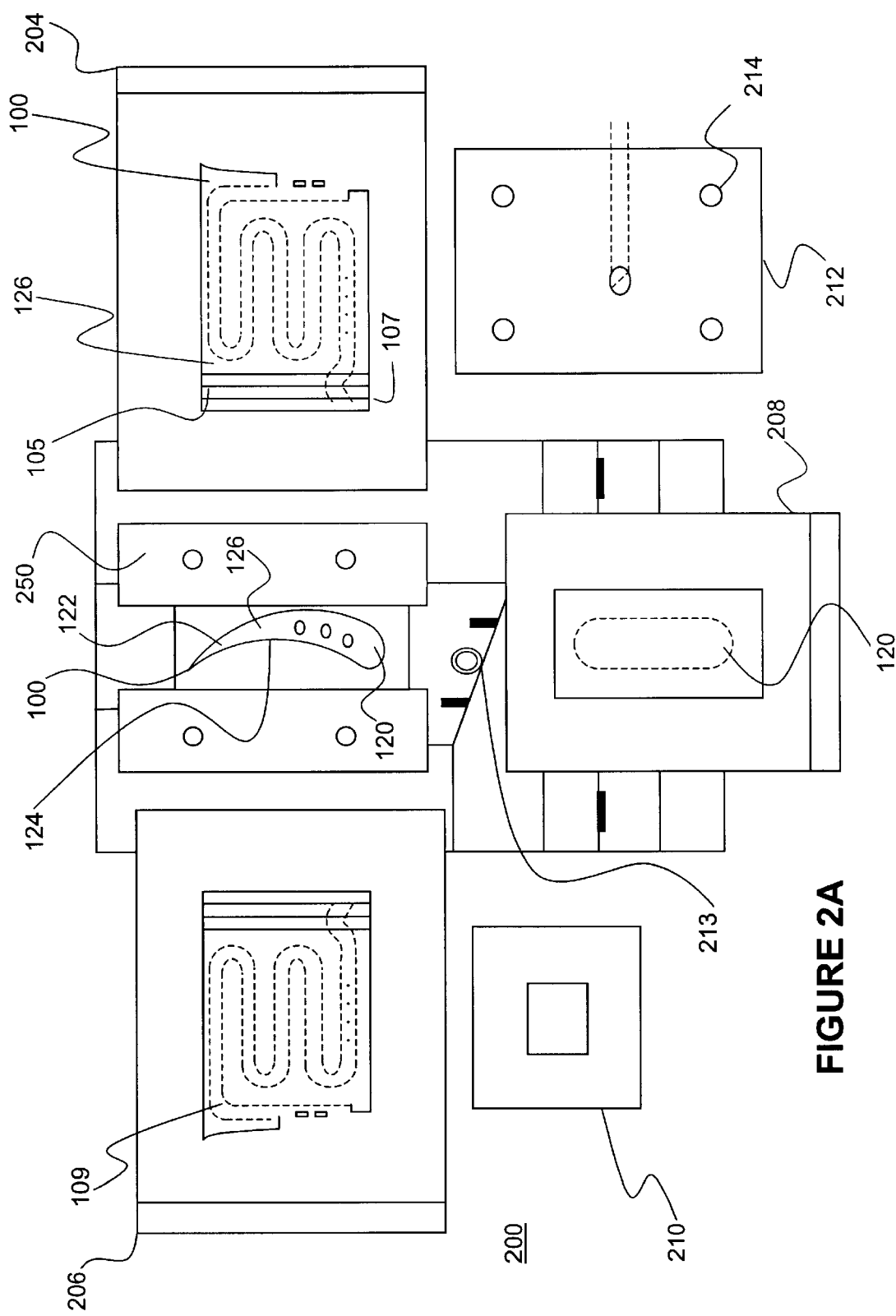
FIGS. 2A–2C illustrate a top view, and two isometric views of an IR inspection apparatus that facilitates simultaneous viewing of more than one side of an inspection article by an IR imager utilizing alternating gases at complementary temperatures, while protecting the IR imager from the alternating temperature gases and debris, in accordance with one embodiment of the present invention.
Figure 2B:
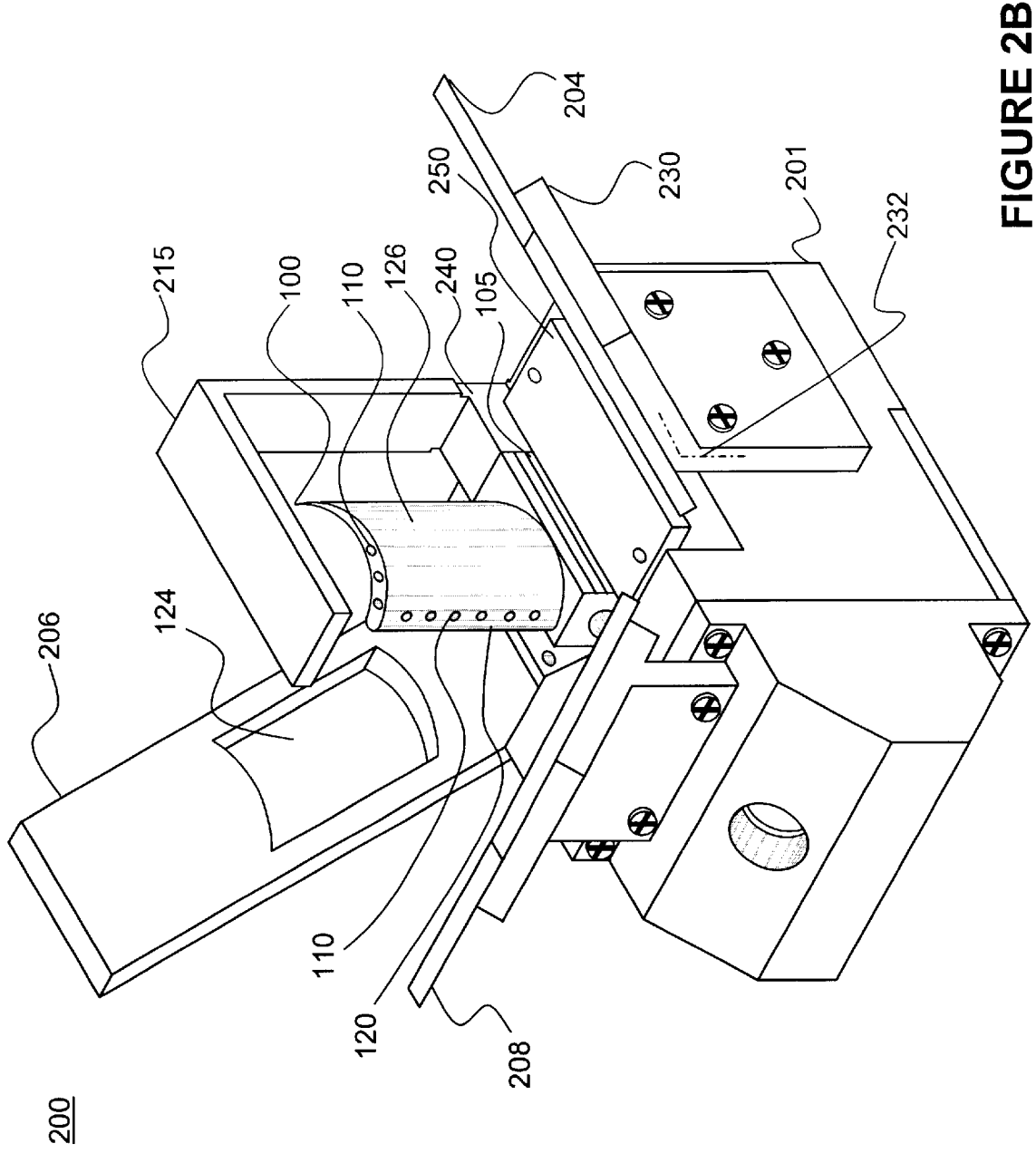
Figure 2C:
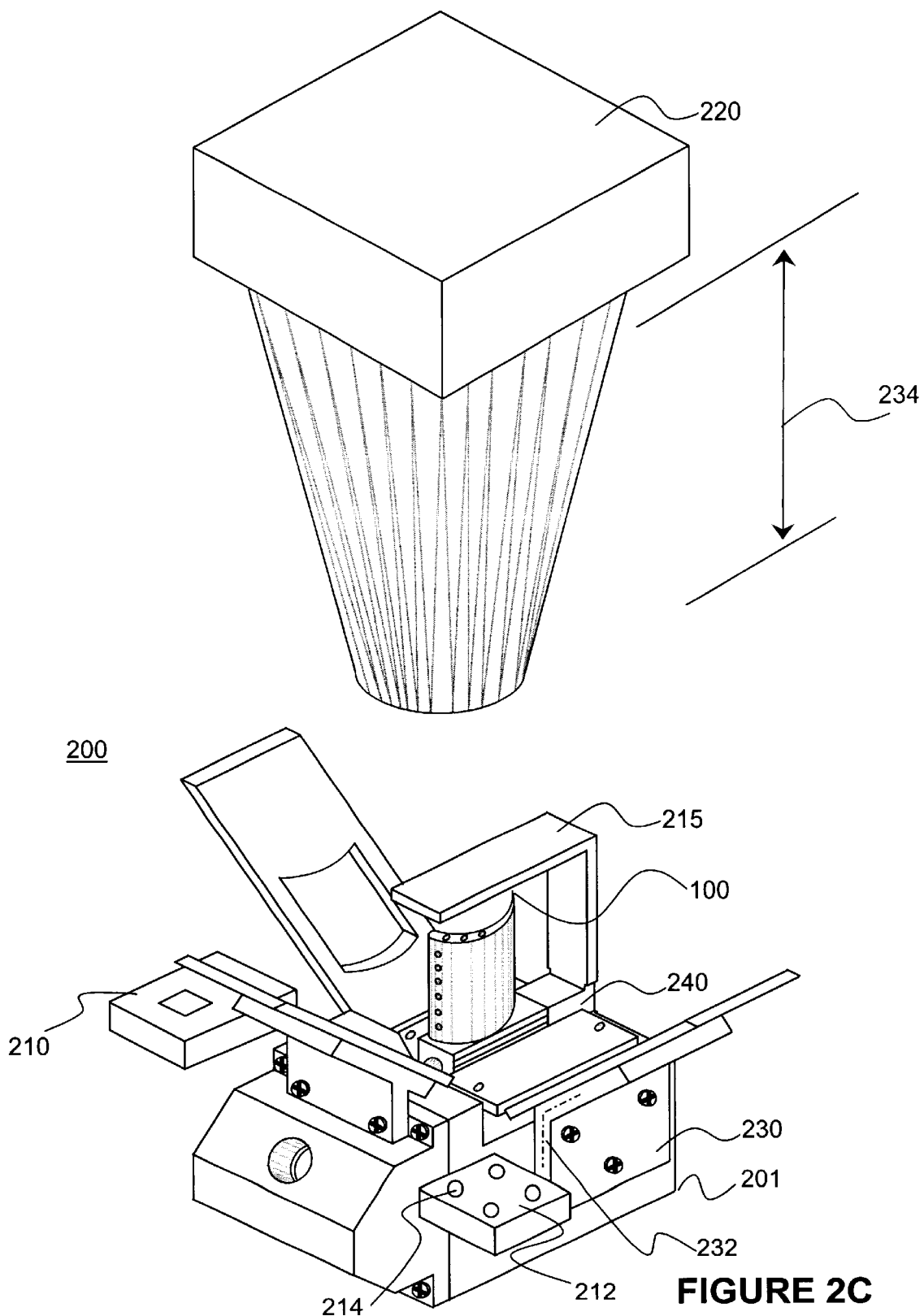

FIGS. 2A–2C illustrate a top view, and two isometric views of an IR inspection apparatus that facilitates simultaneous viewing of more than one side of an inspection article by an IR imager utilizing alternating gases at complementary temperatures, while protecting the IR imager from the alternating temperature gases and debris, in accordance with one embodiment of the present invention. FIG. 2A, the top view, is a view that would be within the field of view of an IR imager 220 (shown in FIG. 2C), of an inspection apparatus 200. The inspection apparatus 200 includes a platform 201, upon which, various components of the inspection apparatus 200 may be successively mounted. Additionally, the platform 201 includes a component holder feature 250 (shown in FIG. 2B) to receive a component, such as, blade 100 for inspection, e.g., the blade base 105 (shown in FIG. 1A).

Mounted on the platform 201 is a first mirror 204 positioned on a first side of the turbine component 100 to reflect an image of the first side of the turbine component 100 during inspection. Mounted on the platform 201 is a second mirror 206 positioned on a second side of the blade 100 to reflect an image of the second side of the turbine component 100 during inspection. Also mounted on the platform 201 is a third mirror 208 positioned on a third side of turbine component 100 to reflect an image of the third side of the turbine component 100 during inspection. In one embodiment shown in FIG. 2A, the first side of the turbine component 100 is the suction side 126 corresponding to the reflected image of the suction side 126 in the first mirror 204. The second side of the turbine component 100 is the pressure side 124 corresponding to the reflected image of the pressure side 124 in the second mirror 206. And finally, the third side of the turbine component 100 is the leading edge 120 corresponding to the reflected image of the leading edge 120 in the third mirror 208. The mirrors may be of any metallic type where the reflection is preferably at least 98% or better.

In various embodiments, mirrors may be manufactured from optically flat glass or quartz coated with protected aluminum or gold.

Shown also in FIG. 2A, are two temperature reference devices, one of which may be a blackbody IR radiation source 210 that can be set and regulated at multiple accurate temperatures, and the other being an ambient temperature reference device 212 that can be unpowered and equilibrates to ambient temperature. The ambient temperature reference device 212 may include four electronic actuated IR emitters 214 that can be used for spatial target calibration. As will be described in further detail below, the two temperature reference devices 210 & 212 and IR emitters 214 are advantageously employed to aid in calibrating the IR imager 220 (shown in FIG. 2C).

Additionally, illustrated in FIG. 2A, is a third temperature reference device, an IR window 213 that facilitates passing of IR radiation at wavelengths acceptable to the IR imager 220 providing information regarding the inspection medium employed to deliver thermal stimulus. In particular, the IR window 213 allows dynamic viewing of the quality of the inspection medium, such as, but not limited to temperature, during inspection of the turbine component 100. Accordingly, inspection medium piped through a thin-walled metal tubing, such as, but not limited to, stainless steel, having an IR emissivity coating, which thermally radiates through the IR window during the inspection of the turbine component. The quality regarding the inspection medium (e.g., gas) aids in calibrating images received by the IR imager 220.

As illustrated in FIG. 2A, the IR imager 220 (shown in FIG. 2C) may simultaneously view two sides, 124 & 126, and two edges 120 & 106 during the inspection.

FIG. 2B is an isometric view illustrating supports 230 that support and thermally isolate the mirrors 204, 206, and 208. For ease of understanding the invention, the three temperature reference devices 210, 212, and 213 will not be shown in FIG. 2B. The supports 230 support the mirrors 204, 206, and 208 such that the mirrors 204, 206, and 208 are at an angle 232 relative to the platform 201. The angle 232 is an angle appropriate to reflect the images of the desired sides of the blade 100 based at least upon a distance 234 (shown in FIG. 2C) of the IR imager 220 (shown in FIG. 2C) from the inspection apparatus 200, where the distance 234 affects the field of view of the IR imager 220. In one embodiment, the distance 234 of the IR imager 220 is such that the angle 232 is 45 degrees to the platform 201. Alternatively, in one embodiment, the angle 232 may be based at least upon a predetermined amount of skewing effect desired for viewing various sides of the blade 100. For example, the third mirror 208 may be at an angle smaller or larger than 45 degrees, such as, but not limited to, 36 degrees relative to the platform 201 facilitating viewing of specific areas of the blade 100 (i.e., the skewing effect).

Shown in FIG. 2B, the supports 230 are mounted; however, alternatively, in one embodiment, the supports 230 may be machined into the platform 201 as grooves having the width and thickness of the mirrors 204, 206, and 208.

Additionally, these machined grooves may have various directions in the platform 201 to facilitate supporting any number of mirrors, such as, but not limited to, seven mirrors to occupy a position every 45 degrees around the inspection apparatus 200.

Additionally, in FIG. 2B, a deflector 215 covers the turbine component 100, shown positioned in the inspection apparatus 200. The deflector 215 protects the IR imager 220 from high temperature gases utilized during inspection and any debris possibly exiting the blade carried by the gases.

FIG. 2C illustrates an isometric view of an inspection apparatus 200 with IR imager 220 and temperature reference devices 210 & 212 shown. Shown in FIG. 2C is the deflector 215 attached to the platform 201 by a hinge 240. The hinge 240 facilitates articulating the deflector 215 in a manner such that the deflector does not interfere with the change-out of the turbine component 100 (i.e., removing an inspected blade and inserting another blade to be inspected) or views of the turbine component 100. Once a new blade is inserted into the inspection apparatus 200, the deflector 215 is articulated into an operating position, as shown in FIGS. 2B & 2C, to protect the IR imager 220 from high temperature gases flowing through the inspection apparatus 200. The deflector may be locked in the operating position by any locking means known in the art, such as, but not limited to, a spring latch or a blade clamp interlock.

Shown in FIGS. 2B–2C, the mirrors 204, 206, and 208 are at an angle of 45 degrees; however, it should be appreciated that the angles may vary and need not be identical between all mirrors, such as, one mirror may be at a different angle from the other mirrors. As previously described, the angle of the mirrors 204, 206, and 208 is based at least upon the field of view of the IR imager 220. Spatial resolution of the IR imager 220 can be based at least upon a working distance (i.e., the closer an object, the improved spatial detail). Accordingly, closer the mirrors 204, 206, and 208 are in relation to the blade 100, smaller the area required to be imaged to capture all views of the blade 100. Thus, the present invention facilitates inspection of very small features, such as, but not limited to, cooling holes 110 and cooling channels 109.

As a result, more than one side of a turbine component may be simultaneously viewed with improved spatial resolution, while protecting an IR imager from alternating gases at complementary temperatures during an inspection of the component.

Referring back to FIG. 2A, the IR detector 220 (shown in FIG. 2C) also captures the IR signatures reference devices 210, 212, 213, and 214. The two temperature reference devices 210 and 212 may have emissivity coatings to facilitate IR radiation to the IR imager 220.

The first temperature reference device, the blackbody IR radiation source 210 may be controlled by software and may be set at various temperatures causing predetermined quantity of IR radiation to be emitted by its surface to calibrate the IR imager 220. The calibration may be performed by ramping temperatures on the blackbody IR radiation source 210 through an IR imager temperature range, and detecting the IR radiation with the IR imager 220. The IR imager temperature range may be based at least upon make and model of the IR imager.

The second temperature reference device, the ambient temperature reference device 212, can be maintained at ambient temperature of the environment surrounding the inspection apparatus 200. The different temperature gases flowing through the inspection apparatus 200 may affect the ambient temperature. Accordingly, maintaining the second temperature reference device 212 at ambient temperature may be facilitated by a number of fans (not shown). The fans draw air from the surroundings for the inspection apparatus 200 and pass the air around the inspection apparatus 200 to be returned to the surroundings. The ambient temperature reference device 212 may include, for example, a resistance temperature detector (RTD) imbedded in its center (i.e., a processor can determine its absolute temperature). As alluded to earlier, the reference devices 210, 212, 213, and 214 may be utilized to calibrate the IR imager 220.

The ambient temperature reference device 212 has four IR emitters 214 that radiate thermal energies when they are activated by the inspection apparatus 200. These IR emitters 214 can be used for spatial alignment of the platform 201 with respect to the IR imager 220. When the IR imager 220 of platform 201 is altered, IR emitters 214 can be used to recalibrate the field of view of the IR imager 220.

In FIG. 2A, the third temperature reference device, the IR window 213, absorbs the temperatures of various inspection media flowing through the inspection apparatus 200 during inspection of the blade 100. Because the IR window 213 can absorb and dissipate heat rapidly, IR window 213 helps to ensure that the inspection medium delivered to the inspection apparatus 200 is precisely at predetermined temperatures. The IR window 213 may be of a material, such as, but not limited to, clear germanium, or fluoride glass.

While the present invention has been described with regard to inspection of gas turbine blades 100 (shown in FIG. 1), it should be appreciated by those skilled in the art that present invention may be practiced to detect defects in any type of internal and/or external features utilizing IR detection methods. Different embodiments and adaptations besides those shown and described herein, as well as many variations, modifications and equivalent arrangements will now be apparent or will be reasonably suggested by the foregoing specification and drawings, without departing from the substance or spirit and scope of the invention. While the present invention has been described herein in detail in addition to its preferred embodiment, it is to be understood that this disclosure is only illustrative and exemplary of the present invention and is made merely for purposes of providing a full an enabling disclosure of the invention.

Thus, an infrared (IR) inspection apparatus that facilitates viewing of more than one side of an inspection object by an IR detector, while protecting the IR from high temperature gases, has been disclosed.

What is claimed is:

1. An apparatus comprising:
   a platform having a turbine component base feature to receive a turbine component for inspection;
   a plurality of mirrors disposed around the turbine component feature on the platform to simultaneously reflect a plurality of sides/edges of the turbine component to an infrared (IR) imager.

2. The apparatus of claim 1, wherein the platform further comprises a plurality of supports mounted on the platform to support the plurality of mirrors.

3. The apparatus of claim 1, wherein the platform further comprises a plurality of slots, machined into the platform, to receive the plurality of mirrors.

4. The apparatus of claim 1, wherein the turbine component is a turbine blade.

5. The apparatus of claim 1, wherein at least one of the plurality of mirrors is a metallic mirror.

6. The apparatus of claim 5, wherein the metallic mirror comprises a metallic mirror having a reflection of at least 98 percent.

7. The apparatus of claim 5, wherein the metallic mirror comprises at least one of a metallic mirror coated with one of protected aluminum or gold.

8. The apparatus of claim 1, wherein the plurality of mirrors comprises a plurality of mirrors that are angularly disposed relative to the platform, to provide a plurality of fields of view for the IR imager.

9. The apparatus of claim 8, wherein the plurality of mirrors further comprises a plurality of mirrors that are angularly disposed relative to the platform, to provide a predetermined amount of skewing effect for the plurality of fields of view for the IR imager.

10. The apparatus of claim 1 further comprising a deflector, disposed between the turbine component and the IR imager to prevent direct exposure of the IR detector to gases flowing through the turbine component and debris exiting the turbine component carried by the gases.

11. The apparatus of claim 10, wherein the deflector is hingedly attached to the platform to facilitate articulation of the deflector during a turbine component change-out.

12. The apparatus of claim 1 further comprising a temperature reference device disposed on the platform to facilitate calibration of the IR imager.

13. The apparatus of claim 12, wherein the temperature reference device comprises a temperature reference device having a thin-walled stainless steel tube with an IR emissivity coating.

14. The apparatus of claim 12, wherein the temperature reference device further comprises a temperature reference device having an IR window to facilitate passing of IR radiation at wavelengths acceptable to the IR imager.

15. The apparatus of claim 14, wherein the IR window comprises an IR window made of one of germanium or fluoride glass.

16. The apparatus of claim 12, wherein the temperature reference device comprises a blackbody IR source.

17. The apparatus of claim 12, wherein the temperature reference device comprises an ambient temperature reference to equilibrate to ambient temperature of a surroundings of the IR imager.

18. An infrared (IR) turbine component inspection apparatus utilizing alternating gases at complementary temperatures comprising:
   a platform having a turbine component base feature to receive the turbine component for inspection;
   a plurality of mirrors, being angularly disposed relative to the platform, around the turbine component feature on the platform to simultaneously reflect a plurality of sides of the turbine component to a IR imager;
   a temperature reference device disposed on the platform to facilitate determination of at least one of a calibration temperature, an ambient temperature, and a blackbody IR radiation source of thermal energies of the alternating gases at different temperatures; and
   a deflector attached to the platform and disposed between the turbine component and the IR imager to prevent direct exposure of the IR imager to alternating gases at different temperatures.

19. The IR turbine component inspection apparatus of claim 18, wherein the platform further comprises a plurality of supports mounted on the platform to support the plurality of mirrors.

20. The IR turbine component inspection apparatus of claim 18, wherein the platform further comprises a plurality of slots, machined into the platform, to receive the plurality of mirrors.

21. The IR turbine component inspection apparatus of claim 18, wherein the deflector is hingedly attached to the platform to facilitate articulation of the deflector during a turbine component change-out.

22. The IR turbine component inspection apparatus of claim 18, wherein the deflector IR turbine component is a turbine blade.

23. The turbine component inspection apparatus of claim 18, wherein the apparatus further comprises the IR imager.

24. Apparatus for infrared (IR) inspection of a gas turbine blade utilizing alternating gases at complementary temperatures, which comprises:
   a platform having a gas turbine blade feature to receive the gas turbine blade for inspection;
   means for simultaneously reflecting a plurality of sides of the received gas turbine blade in the platform to an infrared (IR) imager;
   means for determining at least one of a calibration temperature, an ambient temperature, and thermal energies of the alternating gases; and
   means for deflecting the alternating gases away from the IR imager to prevent direct exposure of the IR imager to the alternating gases.

25. The apparatus of claim 24, wherein the means for simultaneously reflecting comprises a plurality of mirrors disposed around the gas turbine blade feature on the platform.

26. The apparatus of claim 24, wherein the means for deflecting comprises a deflector disposed between the gas turbine blade and the IR detector.

27. The apparatus of claim 24, wherein the means for determining comprises a temperature reference device disposed on the platform.

28. The apparatus of claim 27, wherein the temperature reference device comprises a temperature reference device having a thin-walled stainless steel tube with an IR emissivity coating.

29. The apparatus of claim 27, wherein the temperature reference device further comprises a temperature reference device having an IR window to facilitate passing of IR radiation at wavelengths acceptable to the IR imager.

30. The apparatus of claim 29, wherein the IR window comprises an IR window made of one of germanium or fluoride glass.

31. The apparatus of claim 27, wherein the temperature reference device comprises a blackbody IR source.

32. The apparatus of claim 24 further comprising IR imaging means.

* * * * *